(12) United States Patent
Smith

(10) Patent No.: US 6,615,667 B2
(45) Date of Patent: *Sep. 9, 2003

(54) COMBINED FLOW, PRESSURE AND TEMPERATURE SENSOR

(75) Inventor: Leif Smith, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/022,361

(22) Filed: Dec. 20, 2001

(65) Prior Publication Data

US 2002/0059827 A1 May 23, 2002

Related U.S. Application Data

(63) Continuation of application No. 09/117,416, filed as application No. PCT/SE97/00150 on Jan. 30, 1997.

(51) Int. Cl.[7] .............................. G01L 9/02; G01D 21/00
(52) U.S. Cl. ..................... 73/719; 73/708; 73/866.5
(58) Field of Search ................ 73/715–721, 756, 73/708, 861.47, 866.5

(56) References Cited

U.S. PATENT DOCUMENTS

| 4,023,562 A | 5/1977 | Hynecek et al. ........... 128/2.05 |
|---|---|---|
| 4,274,423 A | 6/1981 | Mizuno et al. ............. 128/675 |
| 4,622,856 A | 11/1986 | Binder et al. ................. 73/727 |
| 4,843,445 A | 6/1989 | Stemme ........................ 357/28 |
| 4,850,358 A | 7/1989 | Millar ........................ 128/637 |
| 4,881,185 A * | 11/1989 | Murakami et al. .......... 702/130 |
| 5,156,052 A | 10/1992 | Johnson et al. ............... 73/727 |
| 5,226,423 A | 7/1993 | Tenerz et al. ............... 128/673 |
| 5,259,248 A | 11/1993 | Ugai et al. ..................... 73/721 |
| 5,404,753 A | 4/1995 | Hecht et al. ............. 73/204.22 |
| 5,447,073 A | 9/1995 | Kalinoski ................ 73/861.24 |
| 5,551,301 A | 9/1996 | Cowan ......................... 73/708 |
| 5,668,320 A | 9/1997 | Cowan ......................... 73/708 |
| 5,715,827 A | 2/1998 | Corl et al. ................... 128/673 |
| 5,728,066 A | 3/1998 | Daneshvar .................... 604/96 |
| 5,761,957 A | 6/1998 | Oba et al. ...................... 73/727 |
| 5,906,636 A | 5/1999 | Casscells, III et al. ........ 607/96 |
| 5,935,075 A | 8/1999 | Casscells et al. ............ 600/474 |
| 6,343,514 B1 * | 2/2002 | Smith ........................... 73/719 |

FOREIGN PATENT DOCUMENTS

| DE | 42 19 454 | 12/1993 |
|---|---|---|
| EP | 0 178 368 | 4/1995 |

* cited by examiner

Primary Examiner—Edward Lefkowitz
Assistant Examiner—Jermaine Jenkins
(74) Attorney, Agent, or Firm—Foley & Lardner

(57) ABSTRACT

The invention relates to a device for measuring pressure, temperature and flow velocity. It comprises a sensor (6) with a sensor support body (13) provided with a diaphragm (15) covering a cavity (14) formed in the support body (13). A pressure sensitive element (41) is mounted on the diaphragm, for recording pressure. Furthermore, a temperature sensitive resistor (42) mounted in the vicinity of and having known temperature dependences, for recording temperature. It also comprises an electrical circuit (43, 44, 45, 46) selectively outputting signals from either of the pressure sensitive element and the temperature sensitive resistor.

17 Claims, 3 Drawing Sheets

COMBINED FLOW, PRESSURE AND TEMPERATURE SENSOR

This application is a continuation of U.S. Application Ser. No. 09/117,416 (filed Apr. 6, 1999), which is the National Stage of International Application PCT/SE97/00150 (which was filed on Jan. 30, 1997, and was published in English on Aug. 7, 1997 as WO 97/27802). This application also claims priority to Swedish Application 9600334-8, filed Jan. 30, 1996. The entire contents of the U.S. application, the PCT application, and the Swedish application are incorporated herein by reference.

The present invention relates generally to pressure, temperature and flow measurements, in particular in the medical field, and especially to in situ measurements of the intracoronary pressure, distally of a stricture, using a guide wire having a pressure sensor mounted at its distal end.

In particular it concerns a combined flow, pressure and temperature sensor.

BACKGROUND OF THE INVENTION

In order to determine or assess the ability of a specific coronary vessel to supply blood to the heart muscle, i.e. the myocardium, there is known a method by which the intracoronary pressure distally of a stricture in combination with the proximal pressure is measured. The method is a determination of the so called Fractional Flow Reserve (see "Fractional Flow Reserve", Circulation, Vol. 92, No. 11, Dec. 1, 1995, by Nico H. j. Pijls et al.). Briefly $FFR_{myo}$ is defined as the ratio between the pressure distally of a stricture and the pressure proximal of a stricture, i.e. $FFR_{myo}=P_{dist}/P_{prox}$. The distal pressure is measured in the vessel using a micro-pressure transducer, and the proximal pressure is the arterial pressure.

A limitation in measuring only the blood pressure and the pressure gradient, alternatively the Fractional Flow Reserve, is that there is no control of the flow in the coronary vessel. As an example, a vessel having a significant stricture would not yield any pressure drop if the myocardium is defective and has no ability to receive blood. The diagnosis will incorrectly show that the coronary vessel is healthy, when instead the conclusion should have been that the myocardium and possibly the coronary vessel are ill.

A diagnosis method for diagnosing small vessel disease is performed as follows:

The Fractional Flow Reserve is determined. If the FFR is <0.75 the coronary vessel should be treated.

If FFR is >0.75 there are two possibilities:

a) either the patient is healthy with respect to the actual coronary vessel (the most plausible), or b) there is a low blood flow distally of the distal pressure measurement due to either an additional stricture or a sickly myocardium.

In order to investigate whether alternative b) is at hand, it is desirable to obtain knowledge regarding the health status of the myocardium, by measuring Coronary Flow Reserve (CFR), or in the alternative the Coronary Velocity Reserve (CVR). The idea is to determine by how many times a patient is able to increase his/her blood flow during work. A healthy patient should be able to increase the blood flow by 2.5–5 times, depending on the patient's age. Work is simulated by the addition of a so called vaso dilating pharmaceutical/medicament, e.g. Adenosine, Papaverin or the like. This medicament dilates the capillaries which increases the blood flow. The same medicament is used for determining FFR.

CFV is defined as $$CFV = Q_{work}/Q_{rest}$$
$$= Q_{during\ vaso\ dilatation}/Q_{rest}$$

(Q is the flow)

This being a ratio and assuming that the cross sectional area is constant during one velocity measurement, it will suffice to measure the velocity.

CFR is defined as $$CFR = Q_{work}/Q_{rest} = [V_{work}*K]/[V_{rest}*K] = V_{work}/V_{rest}$$

Since the desired parameter is a flow increase, it will be sufficient to obtain it as a relative quantity $$CFR = [K*V_{work}]/[K*V_{rest}]$$

wherein K is a constant.

Researchers have devised methods where the pressure and flow velocity in the coronary vessel are measured, the results being presented as so called "pressure-velocity loops". Thereby it becomes possible to distinguish patients suffering from the so called "small vessel disease" from others. In patients with "small vessel disease" the pressure gradient, corresponding to a low FFR, and the velocity of flow will be low, whereas healthy patients will have a low pressure gradient, corresponding to a high FFR, and a high flow.

In some investigations the applicant's system for pressure measurements in vivo, Pressure Guide™ (Radi Medical Systems) and the flow sensor sold under the trade name Flowmap™ (Cardiometrics) have been tested.

It is a great drawback to have to introduce two sensors into the coronary vessel, compared to a situation where both sensors are mounted on a "guide wire". Thus, it has been suggested to provide a guide wire with two sensors, but this presents several technical problems with the integration of two sensors in a thin guide wire.

SUMMARY OF THE INVENTION

The object of the invention is therefor to make available means and methods for carrying out such combined pressure and flow measurements with a single unit, thus facilitating investigations of the outlined type, and making diagnosing more reliable.

The object outlined above is achieved according to the invention with the sensor as described herein, whereby the problems of the prior art have been overcome. The key is to use the temperature sensitive element for obtaining a flow parameter. Thus, there is provided a single sensor having the ability to measure both the pressure and to determine the velocity of flow or the volume flow. A great advantage with such a solution is that only one electrical circuit needs to be provided in a guide wire.

In a preferred embodiment, the sensor is an electrical sensor of a piezoresistive type. However it is contemplated that other pressure sensitive devices may be used, e.g. capacitive devices, or mechanically resonating sensors.

In accordance with the invention there is also provided a method of determining pressure, temperature and flow in a coronary vessel.

Further scope of applicability of the present invention will become apparent from the detailed description given hereinafter.

However, it should be understood that the detailed description and specific examples, while indicating preferred embodiments of the invention are given by way of illustration only, since various changes and modifications within the spirit and scope of the invention will become apparent to those skilled in the art from this detailed description. the invention are given by way of illustration only, since various changes and modifications within the spirit and scope of the invention will become apparent to those skilled in the art from this detailed description.

BRIEF DESCRIPTION OF THE DRAWINGS

The present invention, will become more fully understood from the detailed description given herein below and the accompanying drawings which are given by way of illustration only, and thus not limitative of the present invention, and wherein.

DETAILED DESCRIPTION OF THE INVENTION

Figure 1A:
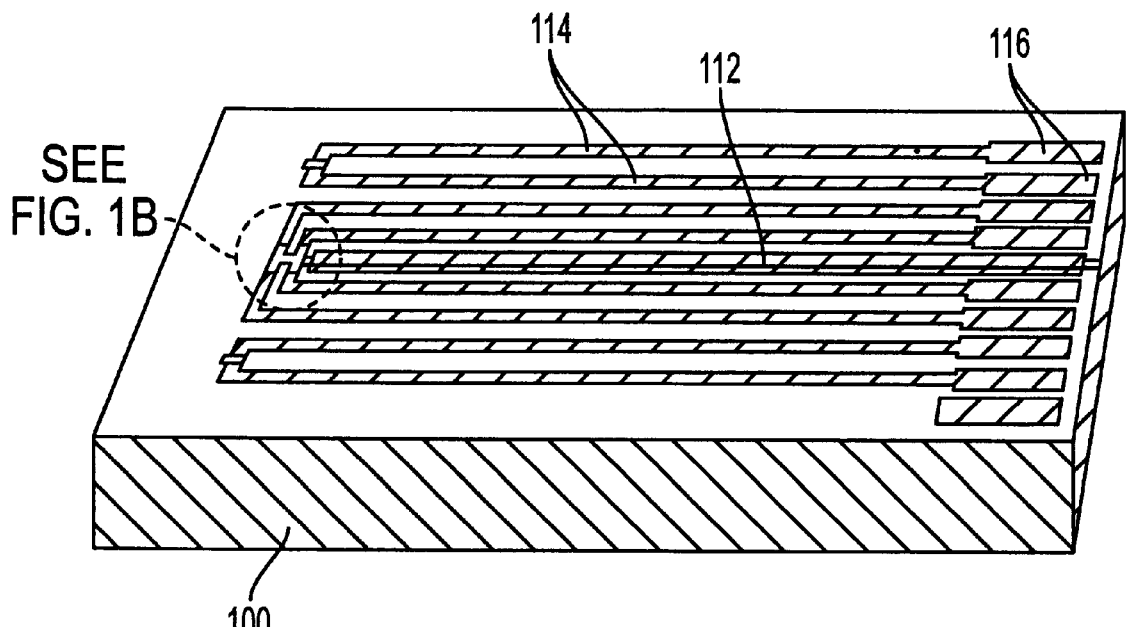
FIGS. 1A and 1B show a microphone for recording extremely small eddies in turbulent gas flows.
Figure 1B:
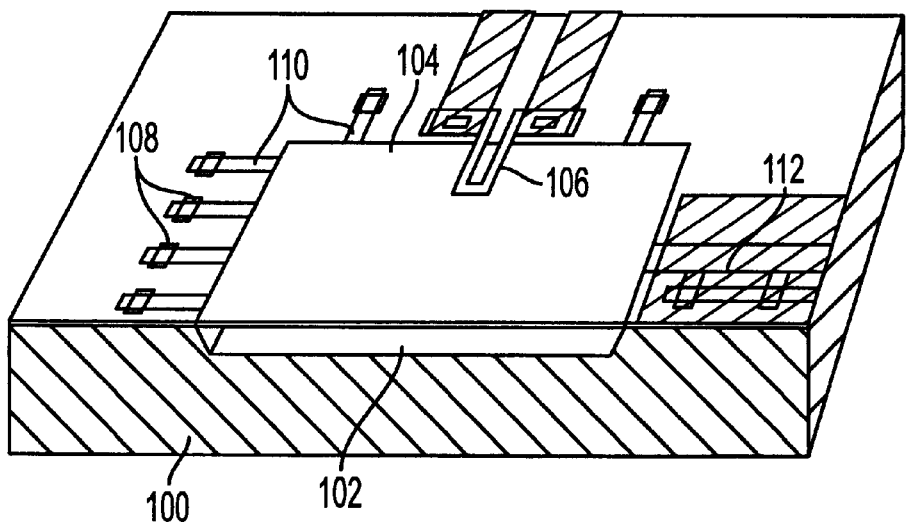

With reference to FIGS. 1a and 1b there is shown a prior art device disclosed in a publication entitled "A Small-Size The microphone comprises a silicon substrate 100, and a cavity 102 in said substrate. A diaphragm of polysilicon 104 covers the cavity 102. On the diaphragm a polysilicon piezoresistor 106 is attached. Etch holes 108 and etch channels 110 are provided for manufacturing purposes. Vent channels 112 are also provided. On the substrate 100 there are metal conductors 114 and bond pads 116 for connecting cabling to external devices.

Figure 2:
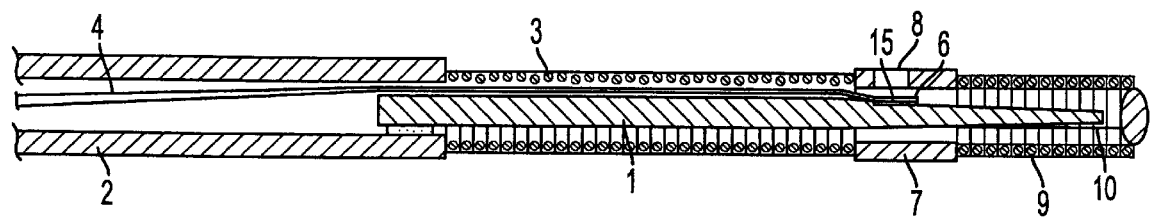
FIG. 2 shows a sensor/guide assembly to be used together with the invention.

Now turning to FIG. 2 there is shown a sensor/guide device comprising a solid wire 1 which is machined by so called centering grinding, and inserted into a proximal tube portion 2. The wire 1 forms the distal portion of the guide, and extends beyond the distal end of the proximal tube portion 2 where said tube is connected to or integrally formed with a spiral portion 3. On the distal end of the wire 1 there is mounted a pressure sensor 6. Between the wire 1 and the spiral portion 3, electrical leads 4 from the electronic circuitry run parallel with said wire 1. The sensor 6 is protected by a short section of a tube 7 having an aperture 8 through which surrounding media act on the pressure sensor. At the very distal end of the entire device there is a radio opaque coil 9, e.g. made of Pt, and used for location purposes, and a safety wire 10 for securing the distal part of the spiral 9.

To minimize the number of electrical leads, the wire or tube may be used as one of the electrical leads.

The proximal tubing 2 and the spiral 3 may be coupled such as to be utilized as an electrical shield, in which case it of course cannot be used as an electrical lead.

Now embodiments of the pressure sensor will be described with reference to FIGS. 3–4.

The sensor is based on the small size silicon microphone mentioned above, which is designed for detecting extremely small eddies in turbulent gas flows. It has been fully described for that application in said publication "Sensors and Actuators A", 1994 (incorporated herein in its entirety by reference). However, it has been modified in accordance with the present invention in the way described below. In order to further miniaturize the external dimensions of the microphone to meet the requirements of the invention, the external dimensions for accommodating the lead pattern on the sensor should be no more than 0.18 mm×1.3 mm×0.18 mm, preferably no more than 0.14 mm×1.3 mm×0.1 mm.

An unexpected advantage of miniaturizing is that the thermal mass, and thereby the thermal time constant, is low, i.e. the entire chip including its resistors heats up and cools down very quickly. In fact it is thereby possible to monitor dynamic changes in the domain 1 Hz and faster. For the purpose of studying flow in blood vessels, the variation of flow velocity or volume flow during a heart cycle is easily detected, and therefor anomalies in the blood flow may be detected.

The sensor (see FIG. 3) comprises a sensor support body in the form of a silicon chip 13 in which there is a cavity 14 made e.g. by etching. Across the cavity there is formed a polysilicon diaphragm 15 having a thickness of e.g. 0.4–1.5 $\mu$m or possibly up to 5 $\mu$m, and a side length of 100 $\mu$m. Within the cavity a vacuum of less than 1000 Pa, preferably less than 30 Pa prevails. In contact with said diaphragm there is mounted a piezoresistive element 41. A pressure acting on the diaphragm 15 will cause a deflection thereof and of the piezoresistive element 41, which yields a signal that may be detected.

In order to attach the cabling 4 to the chip, bond pads 19 are required. These bond pads must have a certain dimension (e.g. 100×75 $\mu$m), and must be spaced apart a certain distance, respect distance approximately 125 $\mu$m. Since the dimensional adaptation entails narrowing the chip, the consequence is that in order to be able to meet the mentioned requirements, the bond pads have to be located in a row, one after the other, as shown in FIG. 3.

It is also preferred for temperature compensation purposes to have a reference resistor 42 mounted on the sensor. This reference resistor 42 may be located on different points on the sensor chip.

In one embodiment it is placed on the diaphragm 15. This is preferred since identical environments to both the active, piezoresistive element 41 and the reference resistor 42 will be provided. Thereby the active element, i.e. the piezoresistive element 41, is mounted such that it will be affected by a longitudinal tension 41 when it is subjected to a pressure. The reference resistor 42 is preferably mounted perpendicularly with respect to the active element 41 and along the border of the diaphragm 15, i.e. at the periphery of the cavity 14 present underneath the diaphragm 15.

However, it is possible to locate the reference resistor on the silicon substrate 13 adjacent the diaphragm. This is an advantage since the reference resistance thereby will be pressure independent.

Another possibility is to locate the reference resistor on a "dummy" diaphragm adjacent the real diaphragm 15, in order to provide the same mechanical and thermal environment for the active element 41 and the reference resistor 42.

Figure 4:
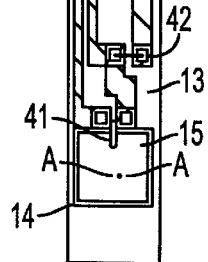
FIG. 4 shows schematically the circuit of a "double" Wheatstone bridge for use in the invention.
Figure 4:
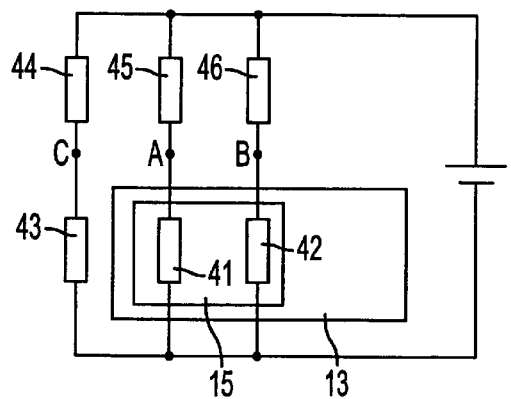

With reference to FIG. 4, an embodiment of the electrical circuit and its operation and function will now be described.

Figure 3:
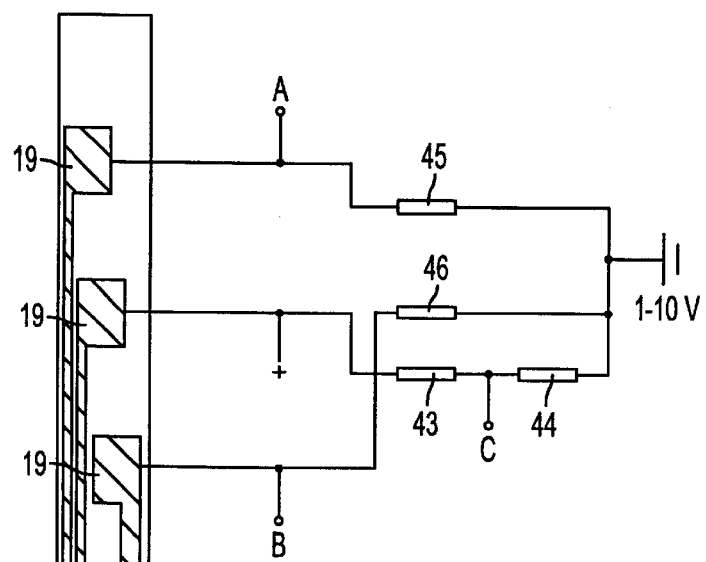
FIG. 3 shows a top view of a pressure sensor chip and the electric circuitry schematically illustrated.

As schematically is shown in FIG. 4, one embodiment of the sensor circuit comprises six resistors 41 . . . 46, two of which 41, 42 are mounted on the diaphragm, as previously mentioned (resistor 41 corresponds to resistor 41 in FIG. 3, and resistor 42 corresponds to resistor 42 in FIG. 3). Resistor 41 is a piezoresistive element, and resistor 42 is only temperature sensitive. The remaining resistors 43, 44, 45, 46 are located externally of the entire sensor/guide assembly, and do not form part of the sensor element.

In this embodiment the resistors are coupled as a "double" Wheatstone bridge, i.e. with resistors 42, 43, 44, 46 forming one bridge (for temperature compensation and flow calculation), resistors 41, 42, 45, 46 forming the second bridge for pressure measurement. Thus, resistors 42 and 46 are shared by the bridges. Thereby it is possible to measure the temperature (across B–C) and pressure (across A–C) independently of each other. From the measured temperature values the flow velocity or volume flow may be calculated.

Figure 5:
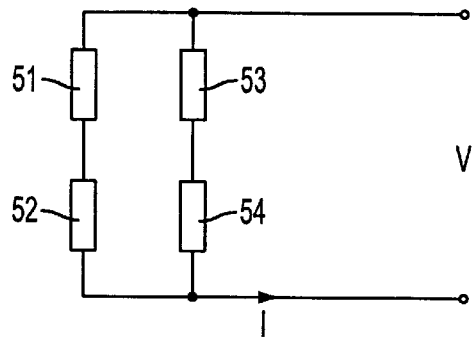
FIG. 5 is an illustration of a Wheatstone bridge used in a second embodiment of the invention.

In another embodiment there are four resistors (51, 52, 53, 54) connected as shown in FIG. 5, i.e. as a simple "single" Wheatstone bridge. If at least one of the four resistors, say 51, has a temperature coefficient $\neq 0$, then temperature changes may be measured as follows:

If the voltage V applied is maintained constant, the current I through the circuit may be measured and is a measure of the temperature, since the total impedance (resistance) of the circuit will change with temperature.

Alternatively the current I may be maintained constant, and in this case the voltage over the bridge will be temperature dependent.

By means of the shown circuit, the CFR can be determined by registering the temperature drop due to a passing liquid having a lower temperature than the body temperature, as will be discussed in detail below.

For the flow determination the principle of so called hot-wire and hot-film anemometers may be employed (reference is made to "Measurement Systems", 3rd edition, pp 506-, by Doebelin, 1983), in which case a flow velocity may be obtained.

Alternatively the principle of thermo-dilution may be employed, in which case the volume flow may be obtained.

Both principles will be discussed below beginning with hot-wire anemometers.

Hot-wire anemometers commonly are made in two basic forms: the constant current type and the constant temperature type. Both utilize the same physical principle but in different ways. In the constant current type, a fine resistance wire carrying a fixed current is exposed to the fluid flowing at a certain velocity. The wire attains an equilibrium temperature when the $i^2R$ heat is essentially constant; thus the wire temperature must adjust itself to change the convective loss until equilibrium is reached. Since the convection film coefficient is a function of flow velocity, the equilibrium wire temperature is a measure of velocity. The wire temperature can be measured in terms of its electrical resistance. In the constant temperature form, the current through the wire is adjusted to keep the wire temperature (as measured by its resistance) constant. The current required to do this then becomes a measure of flow velocity.

For equilibrium conditions we can write an energy balance for a hot wire as $$I^2R_w = hA(T_w - T_f)$$

where

I=wire current $T_w$=wire temperature $T_f$=temperature of flowing fluid h=film coefficient of heat transfer A=heat transfer area $R_w$=wire resistance h is mainly a function of flow velocity for a given fluid density.

It can be written generally on the form $$h = C_0 + C_1\sqrt{V}$$

where V is the flow velocity, and $C_0$ and $C_1$, are constants. For a more detailed account of the theory for hot-wire anemometers reference is made to the cited publication.

In pressure measurement mode the resistors in the circuit (FIG. 4) are supplied with 1–10 V (AC or DC), and the potential difference between A and B is registered as a signal representing the pressure. Unless the resistors 41 and 42 are identical in terms of their temperature dependence, this potential difference will be temperature dependent, i.e. one has to know a quantity representative of the temperature at which the measurement takes place in order to obtain a correct pressure value, and therefore the bridge has to be calibrated. This is achieved by recording the potential difference between A and B (see FIG. 4) as a function of the potential difference between A and C at different temperatures, e.g. in a controlled temperature oven or in a water bath. Thus, an "off set" vs temperature dependence curve is obtained, that is used to compensate the pressure signal (A–B) for a given temperature. Namely, at a given temperature it is known from the calibration curve how much should be subtracted from or added to the actual registered signal in order to obtain a correct pressure. It would be advantageous if resistors 41 and 42 have identical or at least a very similar temperature dependence. This is in fact also the case, since they are made in practice at the same time during manufacture of the chip itself. Thus, material composition and properties are in practice identical. Nevertheless the above outlined compensation is necessary in most cases.

The actual compensation process is built into the software of the electronic system, and implementation thereof requires only ordinary skill.

The inventors have now realized that it is possible to make use of the temperature dependent resistor in a pressure bridge as described above, for flow measurements, using the principle of the hot-wire anemometer.

Thus, the temperature sensitive resistor 42 (FIG. 4) having a known temperature behavior as a function of the current supplied to it, is fed with a current that in a static situation (i.e. no flowing fluid surrounding it) would yield a certain temperature, as reflected in its resistance. If there is a difference in the measured resistance compared to what would have been expected in the static situation (i.e. no flow), it can be concluded that a cooling of the resistor is taking place, and thus that there is a flow of fluid. The measurement is made over B–C in the figure. On the basis of this information, the theory indicated above for anemometers may be applied, and a flow velocity calculated.

The CFR value may be obtained in the following way using the anemometer principle:

1. place a sensor distally of a suspected stricture
2. register the flow parameter ("flow velocity") in a rest condition, $V_{rest}*K$ (K is a constant)
3. inject a medicament (e.g. Adenosin, Papaverin) for vaso dilatation
4. register the flow parameter ("velocity") in a work condition, $V_{max}*K$ (K is a constant)
5. calculate $CFR = V_{max}/V_{rest}$ During the same procedure the FFR (Fractional Flow Reserve) may also be obtained by measuring the distal and proximal pressures and calculating $FFR=P_{dist}/P_{prox}$.

Now the embodiment utilizing the principle of thermo-dilution will be described.

The principle of thermo-dilution involves injecting a known amount of cooled liquid, e.g. physiological saline in a blood vessel. After injection the temperature is continuously recorded with a temperature sensor attached to the tip of a guide wire that is inserted in the vessel. A temperature change due to the cold liquid passing the measurement site, i.e. the location of the sensor, will be a function of the flow (see FIG. 5).

There are various methods of evaluating the temperature signal for diagnostic purposes. Either one may attempt to calculate the volume flow, or one may use a relative measure, where the flow in a "rest condition" is compared with a "work condition", induced by medicaments.

Figure 6A:
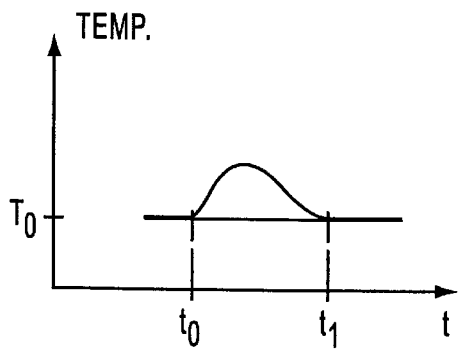
FIGS. 6A and 6B show temperature profiles obtained in a thermodilution type measurement.
Figure 6B:
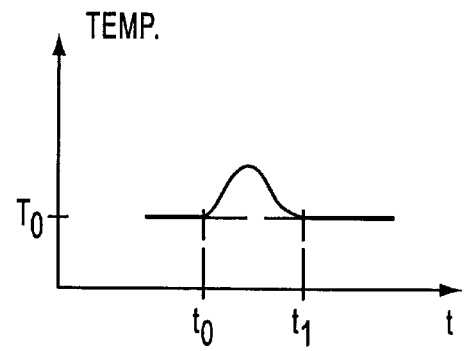

The latter is the simpler way, and may be carried out by measuring the width at half height of the temperature change profile in the two situations indicated, and forming a ratio between these quantities (see FIG. 6).

Figure 7:
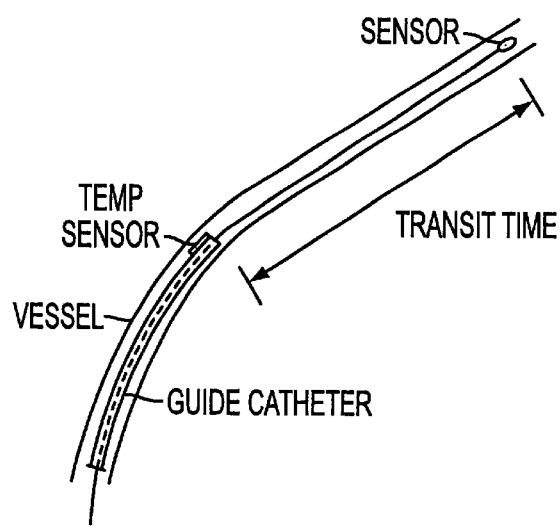
FIG. 7 is a schematic illustration showing how transit time is used to obtain the desired parameter.

Another way of obtaining a ratio would be to measure the transit time from injection and until the cold liquid passes the sensor, in rest condition and in work condition respectively. The relevant points of measurement are shown in FIG. 7.

The former method, i.e. the utilization of the volume flow parameter as such, requires integration of the temperature profile over time (see FIG. 6) in accordance with the equations given below $$Q_{rest} = V \bigg/ \int_{t_0}^{t_1} (T_{r,m}/T_{r,1}) dt \propto V \bigg/ \int_{t_0}^{t_1} (T_{r,0} - T_{r,m}) dt \quad (1)$$

$$Q_{work} = V \bigg/ \int_{t_0}^{t_1} (T_{w,m}/T_{w,1}) dt \propto V \bigg/ \int_{t_0}^{t_1} (T_{w,0} - T_{w,m}) dt \quad (1)$$

wherein

V is the volume of injected liquid $T_{r,m}$ is the measured temperature at rest condition $Tr_{r,1}$ is the temperature of injected liquid at rest condition $T_0$ is the temperature of the blood, i.e. 37° C.

$T_{w,m}$ is the measured temperature at work condition $T_{w,1}$ is the temperature of injected liquid at work condition Q is the volume flow These quantities may then be used directly for assessment of the condition of the coronary vessels and the myocardium of the patient, or they may be ratioed as previously to obtain a CFR, i.e. $CFR=Q_{work}/Q_{rest}$.

A method of diagnosing small vessel disease, using the device of the invention comprises performing measurements at a site in a vessel distally of a suspected stricture. Thus, a pressure sensitive element and a resistor on a sensor element is provided at a measurement site, by inserting through a catheter. The pressure sensitive element and said resistor are part of an electric circuit yielding a pressure indicative output and a temperature indicative output, and have known temperature dependencies. The resistor is used as a reference for the pressure sensitive element. At the site the sensor element will be subjected to flowing fluid, i.e. blood, and the temperature of said fluid is monitored by continuously recording said temperature indicative output from said electric circuit. Then said resistor is subjected to a changed thermal environment. The change in said temperature indicative output resulting from said changed thermal environment is registered. This change in temperature indicative output is used to calculate a flow parameter ($Q_{rest}$). A vaso dilating drug is injected in said vessel to simulate a work condition, and the distal pressure ($P_{work,dist}$) and temperature of said fluid is monitored by continuously recording said pressure indicative output and said temperature indicative output from said electric circuit. Again the resistor is exposed to a changed thermal environment, and the change in said temperature indicative output resulting from said changed thermal environment is registered. A flow parameter ($Q_{work}$) is calculated from said change in said temperature indicative output. The proximal pressure ($P_{prox,work}$) is determined, and $CFR=Q_{work}/Q_{rest}$ and $FFR=P_{dist,work}/P_{prox,work}$ are calculated. Finally the calculated CFR and FFR are compared with corresponding quantities representative of a healthy patient.

The invention being thus described, it will be clear that the same may be varied in many ways. Such variations are not to be regarded as a departure from the spirit and scope of the invention, and all such modifications as would be clear to one skilled in the art are intended to be included within the scope of the following claims.

In particular it may find utility in other areas of the medical field, wherever it is desired to measure pressure, temperature and flow with one single device. It could also be used in non-medical fields.

What is claimed is:

1. A device for biological pressure and temperature measurements, comprising:
   a guide wire;
   a pressure sensor mounted on the guide wire;
   a temperature sensor mounted on the guide wire in the vicinity of the pressure sensor; and
   an electronic circuit to generate and output an indication of temperature based on signals from the temperature sensor, wherein the electronic circuit further outputs an indication of a flow parameter of a flowing fluid based on signals from the temperature sensor.

2. The device as set forth in claim 1, wherein the electronic circuit outputs an indication of the flow parameter while a high current passes through the temperature sensor.

3. The device as set forth in claim 1, wherein the electronic circuit outputs an indication of the flow parameter when the temperature of the temperature sensor is sufficiently different from a fluid temperature of the fluid.

4. The device as set forth in claim 1, wherein the pressure sensor includes a resistor.

5. The device as set forth in claim 1, wherein the pressure sensor is of a piezoresistive type.

6. The device as set forth in claim 1, wherein the pressure sensor is of a capacitive type.

7. The device as set forth in claim 1, wherein the pressure sensor is of a mechanically resonating type.

8. The device as set forth in claim 1, wherein the temperature sensor is temperature sensitive.

9. The device as set forth in claim 1, wherein the temperature sensor includes a resistor.

10. The device as set forth in claim 9, wherein the resistor has a known temperature behavior as a function of current supplied to the resistor.

11. The device as set forth in claim 1, wherein the temperature sensor is pressure independent.

12. The device as set forth in claim 1, wherein a portion of the temperature sensor is exposed to the fluid.

13. The device as set forth in claim 1, wherein the guide wire is configured to be introduced into a vessel of a living body.

14. The device as set forth in claim 1, wherein the fluid is flowing inside a living body.

15. The device as set forth in claim 1, wherein the flow parameter is flow.

16. A device for biological measurements, comprising:

a guide wire;

a pressure sensor mounted on the guide wire; and a flow sensor mounted on the guide wire, wherein the flow sensor is configured to sense a flow of fluid based on a temperature change, wherein the temperature change is indicated by a difference between a measured resistance of the flow sensor and a static resistance of the flow sensor that would be expected when there is no flow.

17. A device for biological measurement, comprising:

a guide wire;

a pressure sensor mounted on the guide wire; and a temperature sensitive resistor mounted on the guide wire, wherein the temperature sensitive resistor is configured to sense a flow of fluid in a vessel of a body based on a temperature change, wherein the temperature change is indicated by a difference between a measured resistance of the resistor and a static resistance of the resistor that would be expected when there is no flow.

* * * * *